(12) United States Patent  (10) Patent No.: US 9,089,675 B2
Schulting  (45) Date of Patent: Jul. 28, 2015

(54) GUIDEWIRE SUPPORT SYSTEM AND GUIDEWIRE

(75) Inventor: Edwin Alexander Schulting, Haren (NL)

(73) Assignee: IMDS R&D BV, Haren (NL)

( * ) Notice: Subject to any disclaimer, the term of this patent is extended or adjusted under 35 U.S.C. 154(b) by 510 days.

(21) Appl. No.: 13/265,910

(22) PCT Filed: Apr. 26, 2010

(86) PCT No.: PCT/NL2010/050233
§ 371 (c)(1),
(2), (4) Date: Dec. 12, 2011

(87) PCT Pub. No.: WO2010/123371
PCT Pub. Date: Oct. 28, 2010

(65) Prior Publication Data
US 2012/0078232 A1   Mar. 29, 2012

(30) Foreign Application Priority Data
Apr. 24, 2009  (EP) .................................... 09158769

(51) Int. Cl.
*A61M 25/00* (2006.01)
*A61M 25/09* (2006.01)
*A61M 29/00* (2006.01)

(52) U.S. Cl.
CPC ............ *A61M 25/09* (2013.01); *A61M 25/0068* (2013.01); *A61M 25/0074* (2013.01); *A61M 29/00* (2013.01); *A61M 2025/0025* (2013.01); *A61M 2025/0081* (2013.01); *A61M 2025/09125* (2013.01); *A61M 2025/09175* (2013.01)

(58) Field of Classification Search
CPC ............ A61M 2025/0183; A61M 2025/09125
USPC .................................................. 600/424, 585
See application file for complete search history.

(56) References Cited

U.S. PATENT DOCUMENTS

| 3,419,010 A | 12/1968 | Williamson |
| 4,531,943 A | 7/1985 | Van Tassel et al. |
| 4,676,249 A | 6/1987 | Arena et al. |

(Continued)

FOREIGN PATENT DOCUMENTS

| EP | 0 823 261 A2 | 2/1998 |
| EP | 1 195 174 B1 | 1/2005 |

(Continued)

OTHER PUBLICATIONS

International Search Report and Written Opinion, dated Jul. 6, 2010, issued in International Application No. PCT/NL2010/050233.

(Continued)

*Primary Examiner* — Sean Dougherty
(74) *Attorney, Agent, or Firm* — Gianna Julian-Arnold; Saul Ewing LLP

(57) ABSTRACT

A guidewire system for insertion into a vascular system of a human or an animal so as to form a guide for guiding a catheter to a predetermined position. The system comprises a support catheter bounding a lumen for receiving at least a portion of the guidewire. The support catheter comprises a guidewire engagement structure for engaging the guidewire inside the lumen. The engagement structure in engaged condition causes the guidewire and the support catheter to be held mutually positioned at least in longitudinal direction thereof.

19 Claims, 3 Drawing Sheets

(56) References Cited

U.S. PATENT DOCUMENTS

| | | | |
|---|---|---|---|
| 4,895,168 A | | 1/1990 | Machek |
| 4,988,356 A | | 1/1991 | Crittenden et al. |
| 5,040,543 A | | 8/1991 | Badera et al. |
| 5,217,434 A | * | 6/1993 | Arney ............... 604/99.04 |
| 5,259,587 A | * | 11/1993 | D'Alessio et al. ............ 251/4 |
| 5,334,187 A | | 8/1994 | Fischell et al. |
| 5,531,689 A | * | 7/1996 | Burns et al. ............ 604/99.04 |
| 5,687,727 A | * | 11/1997 | Kraus et al. ............... 600/434 |
| 5,749,849 A | | 5/1998 | Engelson |
| 5,769,786 A | * | 6/1998 | Wiegel ................... 600/372 |
| 5,830,157 A | * | 11/1998 | Foote ...................... 600/585 |
| 5,919,162 A | * | 7/1999 | Burns .................. 604/99.01 |
| 6,030,349 A | * | 2/2000 | Wilson et al. ............. 600/585 |
| 6,042,578 A | | 3/2000 | Dinh et al. |
| 6,106,487 A | * | 8/2000 | Duane et al. ............. 600/585 |
| 6,231,543 B1 | * | 5/2001 | Hegde et al. ............ 604/96.01 |
| 6,533,772 B1 | | 3/2003 | Sherts et al. |
| 7,087,010 B2 | * | 8/2006 | Ootawara et al. ......... 600/104 |
| 7,717,865 B2 | * | 5/2010 | Boutillette et al. ......... 600/585 |
| 7,886,906 B1 | * | 2/2011 | Dunn ..................... 206/364 |
| 7,922,650 B2 | * | 4/2011 | McWeeney et al. ......... 600/104 |
| 2002/0099397 A1 | | 7/2002 | Sparks |
| 2003/0139689 A1 | | 7/2003 | Shturman et al. |
| 2004/0006329 A1 | | 1/2004 | Scheu |
| 2004/0039372 A1 | | 2/2004 | Carmody |
| 2005/0070820 A1 | * | 3/2005 | Boutillette et al. ......... 600/585 |
| 2005/0096566 A1 | * | 5/2005 | Arnott ..................... 600/585 |
| 2005/0228431 A1 | | 10/2005 | Meguro et al. |
| 2006/0135948 A1 | * | 6/2006 | Varma ...................... 604/523 |
| 2007/0021685 A1 | * | 1/2007 | Oepen et al. ............... 600/585 |
| 2007/0118079 A1 | * | 5/2007 | Moberg et al. .......... 604/164.07 |
| 2007/0161969 A1 | * | 7/2007 | Andersen ................... 604/533 |
| 2007/0270755 A1 | * | 11/2007 | Von Oepen et al. ..... 604/164.13 |
| 2007/0293719 A1 | * | 12/2007 | Scopton et al. ............ 600/106 |
| 2009/0124934 A1 | * | 5/2009 | Rabbitte et al. ............ 600/585 |
| 2009/0259285 A1 | | 10/2009 | Duane et al. |
| 2010/0191152 A1 | * | 7/2010 | Boutillette et al. ........... 600/585 |
| 2010/0198056 A1 | * | 8/2010 | Fabro et al. ................ 600/424 |

FOREIGN PATENT DOCUMENTS

| | | |
|---|---|---|
| EP | 1 526 889 B1 | 12/2009 |
| WO | 93/06878 | 4/1993 |
| WO | 02/074378 A3 | 9/2002 |
| WO | 2004/026387 A1 | 4/2004 |
| WO | 2007/058816 A3 | 5/2007 |
| WO | 2007/139457 A1 | 6/2007 |
| WO | 2010/078335 A1 | 7/2010 |

OTHER PUBLICATIONS

European Search Report, dated Sep. 23, 2009, issued in priority Application No. 09158769.1.

Presentation "Patient with CTO, how to approach in 2007" by Dr. Nicolaus Reifart; member of the EU CTO club during EURO PCR Barcelona 2007.

Presentation "Cutting edge devices for treating CTO" by Dr. Nicolaus Reifart; member of the EU CTO club during EURO PCR Barcelona 2007.

Ochiai, Masahiko, Division of Cardiology and Cardiovascular Surgery, Showa University Northern Yokohama Hospital, Yokohama, Kanagawa, Japan "Retrograde approach for chronic total occlusion: present status and prospects"—EuroIntervention 2007:3:169-173.

Bishop, Arthur F. et al. "Antegrade Selective Catheterization of the Superficial Femoral Artery Using a Movable-Core Guide Wire"—Radiology, Nov. 1985.

Dehlagi, Vahab et al. "Effect of Stent Geometry on Phase Shift between Pressure and Flow Waveforms in Stented Human Coronary Artery"—American Journal of Applied Sciences 5 (4): 340-346, 2008.

\* cited by examiner

GUIDEWIRE SUPPORT SYSTEM AND GUIDEWIRE

CROSS REFERENCE TO RELATED APPLICATIONS

This application claims the priority of PCT/NL2010/050233, filed on Apr. 26, 2010, which claims the benefit of priority to European Application No. 09158769.1, filed on Apr. 24, 2009, the entire contents of which are hereby incorporated in total by reference.

FIELD AND BACKGROUND OF THE INVENTION

The invention relates to a system for supporting a guidewire that is advanced towards a predetermined position in a vascular system of a human or an animal.

Percutaneous coronary intervention procedures are used to treat patients with diseased arteries of the heart such as stenosis caused by a build-up of fats, cholesterol and other substances from the blood (referred to as plaque) that severely restricts or (almost) blocks blood flow.

PCI may be performed by threading a catheter, along a path previously defined by bringing a guidewire to the position of the stenosis, from an artery in the groin to a position in an artery of the heart. This is known as percutaneous transluminal coronary angioplasty (PTCA), coronary artery balloon dilation or balloon angioplasty. The balloon is then inflated, compressing the plaque and dilating (widening) the narrowed coronary artery so that blood can flow more easily. To maintain the dilated section of the blood vessel open, an expandable metal stent may be expanded by the inflating balloon and left in place as the balloon is retracted after deflation.

In the event of a heart attack, it may be required that the blocked artery is opened quickly by inflating a small balloon and inserting a stent to restore blood flow to the heart muscle within 90 minutes of the patient's arrival at the hospital. PCI in such emergency circumstances is referred to as "primary" PCI. Other PCI procedures, such as those done to unblock an artery before a heart attack occurs, are referred to as "elective" PCI.

The number of complex stenotic lesions to be treated is growing. At present, about 25% of the PTCA treatments involves the treatment of such complex stenotic lesions. Complex lesions are for instance lesions with calcification, lesions that are far from the point of entry into the patient and diffuse lesions of which the boundaries are difficult to locate precisely.

Passing a guidewire through a complex stenotic lesion (also referred to as crossing of the lesion) is one of the larger challenges for interventionists. Crossing complex lesions involves two main problems: safety of the patient and costs of the treatment.

For crossing non-complex stenotic lesions, a guidewire having a soft and/or flexible tip is used. Because of the flexibility of the tip, the risk of causing complications, such as perforation of the wall of the vessel is small. However, crossing a complex stenotic lesion conventionally requires the use of a guidewire having a more rigid tip; the more complex the lesion, the more stiff and/or sharp the tip of the guidewire needs to be to successfully cross the lesion. A disadvantage of a guidewire having a stiff tip is that it is more difficult to navigate the guidewire through tortuous vascular sections.

Cardiologists use contrast liquid and X-ray imaging to obtain a fluoroscopic image of the structure of the coronaries of a patient. During the procedure contrast liquid needs to be injected at regular intervals to maintain good vision during the procedure, especially during complex procedures. However, it is in the interest of the patient's safety to keep dosages of contrast liquid and X-ray radiation low. Repeated exposure to stray levels of X-ray radiation also constitutes a hazard for medical personnel.

The safety of the patient is also related to the duration of the procedure. The longer the procedure, the higher the risk of complications, such as the formation of thrombosis on the devices inserted into the patient. Complex procedures generally take substantially more time than straightforward procedures and therefore inherently entail an increased risk of complications.

Treatment of a complex stenotic lesion requires a cautious approach involving the introduction of several guidewires before a lesion can be crossed. On average, the time required for crossing a complex stenotic lesion constitutes more than 80% of the overall duration of the procedure while the available amounts of time of catheterization facilities and cardiologists is typically limited. Thus, longer procedure times directly affect costs and the duration of waiting periods for patients to be treated.

For instance, although chronic total occlusions (CTOs) are frequently found in patients who undergo coronary arteriography for known or suspected coronary artery disease, only a few of these lesions (5.7-9.4%) are treated by PCI. The reason for this low number may be due to the low success rate of PCI, as well as the high procedural cost and high radiation exposure for both patients and operators (J. D. Abbott et al.; *Recent trends in the percutaneous treatment of chronic total coronary occlusions*; Am J. Cardiol. 2006; 97:1691-6). The most common reason that PCI fails in patients with CTO is the inability to pass a guidewire across the occlusion into the distal vessel (M. Ochiai; *Retrograde approach for chronic total occlusions: present status and prospects*; EuroInterv. 2007:3:169-173). An increased success rate in the treatment of CTOs would result in applicability of PCI to a larger number of cases.

In view of the increasing numbers of treatments of complex stenotic lesions and the problems regarding patient safety, costs and, in some countries, waiting time, there is an important need for solution which allows to cross complex lesions more safely and more quickly. Current specialized methods for the treatment of complex stenotic lesions have seen limited success and are not suitable for the average cardiologist.

Similar problems arise in the crossing of constrictions or occlusions in the course of percutaneous treatment of other endovascular diseases and neurovascular disease treatment.

SUMMARY OF THE INVENTION

It is an object of the present invention to provide a solution which generally allows to cross complex constrictions or occlusions in a vascular system of a patient more safely and more quickly and/or allows to cross more difficult constrictions and occlusions.

According to the invention, this object is achieved by providing a guidewire support system according to claim 1. The invention can also be embodied in a guidewire according to claim 18, which is specifically adapted for use with particular embodiments of a guidewire support system according to the invention.

The guidewire engagement structure for allowing the support catheter to engage the guidewire allows entraining the support catheter with the guidewire and/or vice versa, which allows to exert a relatively large force onto a lesion as well as to protect the flexible tip of the guidewire against damage, such as permanent deformation due to buckling by holding it in a partially or fully retracted position when a projecting position is not desired or would entail a particular risk of damaging the tip. The position of the distal ends of the support catheter and the guidewire relative to each other in longitudinal direction can be controlled easily, so that crossing of complex lesions can be performed relatively quickly.

Particular elaborations and embodiments of the invention are set forth in the dependent claims.

Further features, effects and details of the invention appear from the detailed description and the drawings.

DETAILED DESCRIPTION

Figure 1:
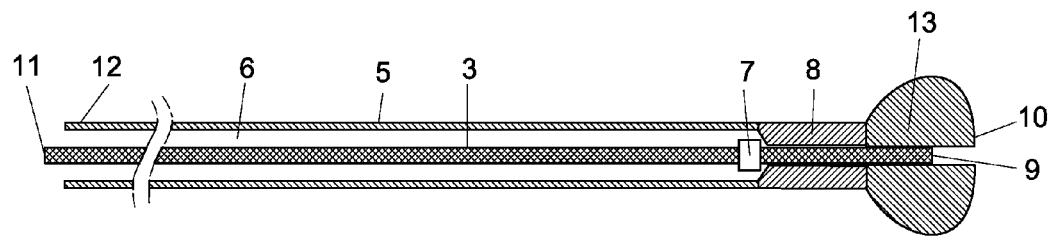
FIG. 1 is a side view in cross-section of a first example of a guidewire system according to the invention.
Figure 2:
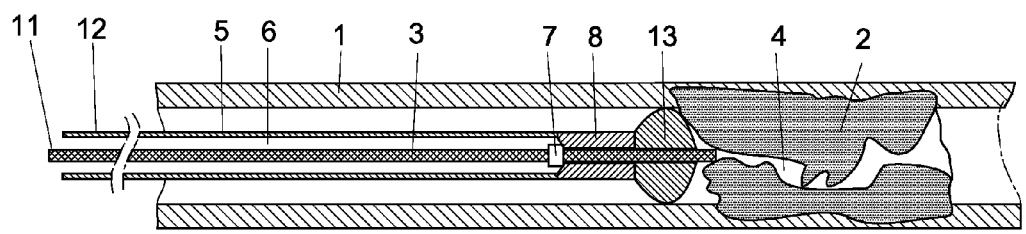
FIG. 2 is a side view in cross-section of a guidewire system according to FIG. 1 in a first operating condition in a blood vessel.
Figure 3:
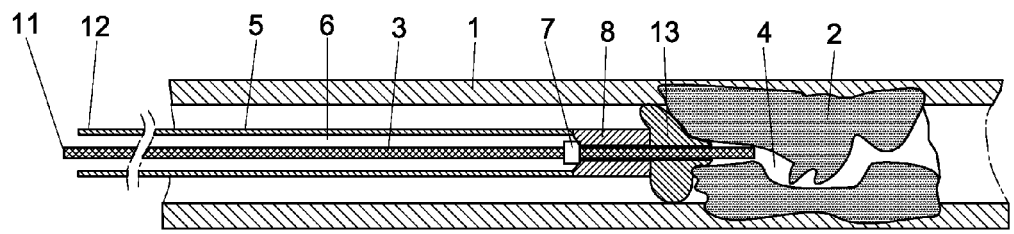
FIG. 3 is a side view in cross-section of a guidewire system according to FIG. 1 in a second operating condition in a blood vessel.

In FIGS. 1-3, a first example of a guidewire system including a guidewire support system according to the invention is shown. The guidewire system is designed for insertion into a vascular system of a human or an animal so as to form a guide for guiding a catheter to a predetermined position. In FIGS. 2 and 3, a blood vessel section 1 constituting a portion of a vascular system of a human or an animal is shown schematically. In the blood vessel 1 a complex lesion 2 (also shown schematically) has formed, leaving a stenosis 4, constituting restricted passage through the lesion 2.

Percutaneous transluminal coronary angioplasty includes bringing a balloon of a balloon catheter in a position inside the stenosis 4 and inflating the balloon so that the stenosis 4 is dilated and, after the balloon has been removed from the location of the stenosis 4, blood flow is no longer or at least substantially less restricted by the lesion 2. The balloon catheter may also be used to bring a stent into the stenosis and expand the stent by inflating the balloon. After having been expanded, the stent will constitute a scaffolding counteracting the lesion to close again. The stent may be provided with a drug-eluting structure counteracting restenosis.

A typical angioplasty procedure would involve initially bringing a guidewire and then a guiding catheter into a position with a distal end co-axial with and lodged in the ostium of a main coronary artery and then retracting the guidewire.

Next, a guidewire is inserted into the vascular system to serve as a guide for guiding a balloon catheter to the location of the stenosis. As the guidewire is inserted, at bifurcations in the coronary vascular system, the leading distal tip of the guidewire, which is slightly curved when in unloaded condition, is steered towards the stenosis 4. To allow navigating of the guidewire to and through the stenosis 4, fluoroscopy, which includes the introduction of contrast liquid to make the blood vessels through which the guidewire is to be passed visible and irradiation with X-ray radiation, is used to obtain an image of the relevant portion of the vascular system and the guidewire. The guidewire, or at least its tip, is made of a radiopaque material, which is visible in a fluoroscopic image. Both the dosage of contrast liquid and X-ray irradiation should be minimized in the interest of the health of the patient. Use of X-ray radiation should also be minimized in the interest of the safety of medical personnel in the vicinity of the patient, for instance the interventionist operating the guidewire.

As can be seen in FIGS. 2 and 3, the remaining passage 4 through the lesion 2 includes a multitude of curves and leaves no straight line through the passage clear from the walls of the passage. Such a lesion 2 is generally referred to as a complex lesion, because it is difficult to pass a guidewire across the lesion 2. Other factors that may be encountered and that cause a lesion to be complex, in the sense that it is difficult to pass a guidewire therethrough, are calcification of the lesion causing the lesion to be relatively inflexible and remoteness of the lesion making it difficult to exert axial force.

The guidewire system shown in FIGS. 1-3 includes a guidewire 3 and a support catheter 5 bounding a lumen 6 for receiving at least a portion of the guidewire 3. For cardiovascular applications, the support catheter may for instance have a length of about 1.0-1.6 m, of which a most distal portion of 0.1 to 1.2 m may be more flexible than a remaining proximal portion, the diameter of the guidewire support catheter is preferably 0.6 to 1.2 mm and the diameter of the guidewire is preferably 0.011" to 0.018" (inch). The guidewire 3 has a support catheter engagement structure 7 for engaging the support catheter 5 inside the lumen 6 and the support catheter 5 has a guidewire engagement structure 8 for allowing it to engage the guidewire 3 inside the lumen 6. The engagement structures 7, 8 in engaged condition cause the guidewire 3 and the support catheter 5 to be mutually positioned in longitudinal direction thereof.

The guidewire engagement structure is constituted by a restriction 8 of the lumen 6 of the support catheter 5 and the support catheter engagement structure is constituted by an abutment 7 projecting transversely from the guidewire 3 and arranged for engaging the restriction 8 in the longitudinal direction.

The support catheter 5 provides lateral support to the guidewire 3 and allows to exert large axial pushing forces at the tip of the guidewire 3, because buckling of the guidewire 3 and the exertion of forces by the guidewire against walls of the vascular system is counteracted. If the abutment 7 engages the restriction 8, the guidewire 3 moreover pulls the support catheter 5 forward, so that also the support catheter 5 can exert relatively large axial forces against the lesion 2 without entailing the exertion of large transversal pressure forces against the walls of the vascular system.

Because the mutual positions of the guidewire 3 and the support catheter 5 in longitudinal direction are predetermined if the engaging structures 7, 8 are in mutual engagement, the relative positions of distal ends 9, 10 of the guidewire 3 and the support catheter 5 are controlled easily so the guidewire 3 and the support catheter 5 can be maneuvered relatively quickly by operating proximal end portions 11, 12 of the guidewire 3 and the support catheter 5 and the risk of permanent deformation of the tip portion of the guidewire 3 is reduced.

Furthermore, friction of the guidewire 3 against vascular walls during rotation of the guidewire 3 about its longitudinal axis for steering purposes is counteracted. If the rotation is imparted to the support catheter 5 that is clamped to the guidewire 3 outside the patient (e.g. as in FIGS. 8-10 which are discussed hereinafter), the support catheter 5 rotates with the guidewire 3. Because of its relatively large diameter, the support catheter is relatively stiff against torsional deformation. The outer surface of the catheter is preferably hydrophilic so the catheter encounters very little resistance when rotating relative to inner surfaces of vascular walls.

In the example shown in FIGS. 1-3, the abutment 7 engages the restriction 8 on a proximal side of the restriction 8. This causes the distance over which the guidewire 3 can be fed in distal direction relative to the support catheter 5 to be limited to a predetermined position shown in FIGS. 2 and 3. The distance over which the guidewire projects from the tip of the catheter when the abutment is in engagement with the restriction is preferably less than 2 cm and more preferably less than 1 or 0.5 cm. After the support catheter 5 has been brought in engagement with the lesion 2 or at least near the lesion, the guidewire 3 can be pushed in distal direction safely without risking that the tip of the guidewire 3 projects too far, which would entail an increased risk of penetration of the wall of the vessel 1. After the material of the lesion has been displaced by the tip 9 of the guidewire 3, the tip 10 of the support catheter 5 can be advanced and thereafter, the tip of the guidewire 3 can be pushed to its most distal position relative to the support catheter 5 again. In many cases, this action can be repeated quickly and safely for the outer ends of the lesion, which tend to be harder than the central portion of the lesion, until the lesion 2 has been passed by at least the tip 9 of the guidewire 3. Because the maximum distance over which the guidewire 3 projects from the distal end of the support catheter 5 is quite limited (a distance of 2-3 mm is usually sufficient to penetrate the outer "cap" of a lesion), the guidewire is very effectively supported against buckling and relatively large forces can be exerted by a relatively flexible guidewire tip.

It is also possible to advance the guidewire 3 and the support catheter 5 simultaneously. In particular if the guidewire 3 and the support catheter 5 are advanced simultaneously the maximum distance over which the guidewire projects from the support catheter is limited particularly effectively. The more simultaneous the support catheter 5 is advanced together with the guidewire, the better the wall of the vessel 1 is shielded from relative motion of the guidewire over the blood vessel wall. Passing the support catheter 5 through the passage 4 furthermore provides the advantage that the stenosis is pre-dilated further than if only a guidewire is passed through the stenosis, so the introduction of a catheter in a next step of the procedure is facilitated.

The support catheter 5 has a distal end portion constituted by a deformable member 13 of a material softer than adjacent more proximal portions of the support catheter 5. When pushed against a lesion 2, the deformable member 13 is axially compressed, causing its cross-sectional size perpendicular to the longitudinal axis of the support catheter 5 to increase. This causes the support catheter 5 and accordingly the distal end of the guidewire 3 to be centered relative to the blood vessel 1 so that the risk of damaging the wall of the vessel 1 is reduced.

In non-deformed condition, the deformable member 13 has an outer cross-sectional contour larger than the cross-sectional contour of a proximally adjacent portion of the support catheter. This is advantageous for centering the tip of the guidewire relative to the vessel. A particularly effective centering can be achieved if the diameter of the deformable member is at least 1.5 or, more preferably, two times the diameter of a proximally adjacent portion of the support catheter.

The deformable member 13 is preferably of natural and/or synthetic elastomeric material having a hardness of less than 60 Shore A and more preferably less than 40 Shore A or 30 Shore A. However, it is also possible to use a harder material, for instance in combination with a hollow or thin-walled design, which may be provided with pleats or a wavy profile to facilitate deformation.

Preferably, the deformable member or another portion of the catheter at or near the distal tip is radiopaque, for instance by being made of radiopaque material or by containing a radiopaque marking element or a radiopaque filler material.

Although the deformable member 13 is particularly advantageous in a guidewire system including an engagement structure for holding the guidewire in a predetermined longitudinal position relative to the support catheter, a deformable member at a distal end of a support catheter can also be advantageously in combination with a conventional guidewire/support catheter combination without an engagement structure for holding the guidewire in a predetermined longitudinal position relative to the support catheter.

If the deformable member 13 is in uncompressed condition and the abutment 7 contacts the restriction 8, the distal end 9 of the guidewire is inside the deformable member 13. Thus, the deformable member 13 shields the tip of the guidewire 3 reducing the risk of damaging the vascular system, yet allows the tip to flex when passing through curved sections of the vascular system towards a lesion.

The deformable member 13 is elastically compressible in longitudinal direction to such an extent that, while the abutment 7 contacts the restriction 8, the distal end 9 of the guidewire 3 projects from the deformable member 13. This allows a relatively large local pressure to be exerted onto a lesion 2 to be passed. Preferably, a desired elastic deformation of the member is obtained in response to a force exerted to or adjacent to the proximal guidewire end of 0.2 to 0.5 N.

The abutment 7 and the restriction 8 are located closely adjacent to the distal ends 9, 10 of the guidewire 3 and, respectively, the support catheter 5. This is advantageous for accurately controlling the relative positions of the distal ends 9, 10 of the guidewire 3 and the support catheter 5. Moreover, since the lumen 6 is relatively wide for allowing the abutment to pass therethrough, contrast liquid can be fed through the lumen 6 with relatively little pressure. Because the distal end of the support catheter is located close to the tip of the guidewire, very small dosages of contrast liquid are sufficient to make portions of the vascular system that are relevant for navigation visible. Conventionally, contrast liquid is fed via the guiding catheter of which the distal end is located more remotely from the distal tip of the guidewire (at the ostium of a main coronary artery) so that larger volumes of contrast liquid are required to obtain the required contrast in the vicinity of the tip of the guidewire.

Figure 4:
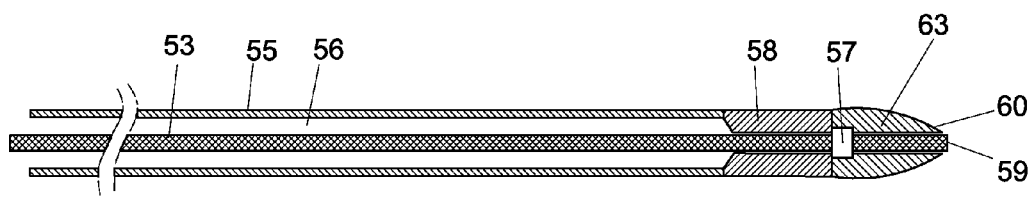
FIG. 4 is a side view in cross-section of a second example of a guidewire system according to the invention.
Figure 5:
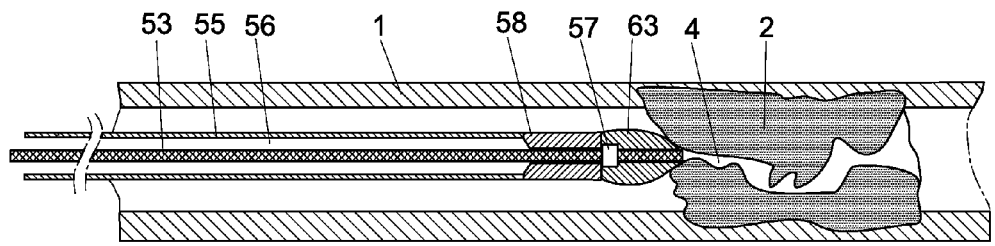
FIG. 5 is a side view in cross-section of a guidewire system according to FIG. 2 in a first operating condition in a blood vessel.
Figure 6:
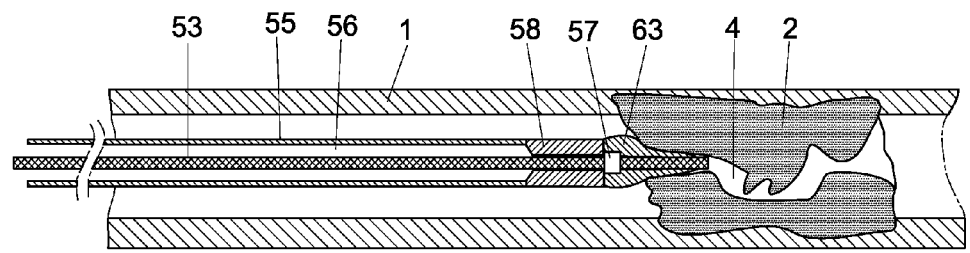
FIG. 6 is a side view in cross-section of a guidewire system according to FIG. 2 in a second operating condition in a blood vessel.

In FIGS. 4-6 an example of a guidewire system according to the invention is shown in which the support catheter shown in FIGS. 1-3 is combined with a different guidewire 53. In this example, the abutment 57 of the guidewire 53 engages the restriction 58 on a distal side of the restriction 58. This allows the guidewire 53 to be introduced prior to the support catheter 55 and to retract the support catheter 55 while leaving the guidewire 53 in place.

When the lesion 2 has to be crossed, the support catheter 55 is advanced against the lesion 2 and centering of its distal end 60 relative to the blood vessel 1 is enhanced by the increased cross-sectional size of the deformable member 63 as it is axially compressed by the axial forces exerted thereon. The position of the distal end 59 of the guidewire 53 relative to the support catheter is easily controlled by the engagement of the abutment 57 and the restriction 58. Accordingly, as the guidewire 53 is subsequently displaced distally out of the support catheter 55 over a given distance from a position in which the abutment 57 abuts against the distal end of the restriction 58, the distance over which a distal end portion of the guidewire 53 projects from the support catheter 55 is easily controlled without having to rely on fluoroscopy. The distance over which the guidewire 53 can be advanced in distal direction relative to the support catheter 55 is not limited by the abutment 57 contacting the restriction 58. Accordingly, the distance over which the guidewire 53 is each time advanced can be adapted to resistance encountered from the lesion 2. If a portion of the passage 4 is relatively straight and/or a portion of the lesion 2 is soft, the guidewire 53 can be advanced over a relatively large distance. This reduces the time required for passing through a lesion 2.

Furthermore, the support catheter 5 can be used to directly transfer a pushing force in longitudinal direction to the distal end portion of the guidewire 53 via the abutment 57. A pulling force may be exerted onto the guidewire 53 if it is desired to keep the abutment 57 in contact with the restriction 58. Thus, by pushing the guidewire 53 out of the support catheter 55, the distal end portion of the guidewire system is very flexible and by pushing the restriction 58 against the abutment 57, the distal end portion becomes stiff an suitable for exerting a relatively large pushing force onto a lesion for pushing the distal end portion through the lesion.

In the example shown in FIGS. 4-6, the deformable member 63 has a smaller diameter than the deformable member 13 shown in FIGS. 1-3 to facilitate passing through narrow passages. The distance between the abutment 57 and the distal end 59 of the guidewire 53 and the distance between the distal side of the restriction 58 and the distal end 60 of the support catheter 55 are related such that the distal end 59 of the guidewire 53 is just outside the support catheter 55 if the deformable member is in undeformed condition. Depending on the situation at the lesion 2 to be treated, requirements regarding the level of cautiousness may vary. For instance, a guidewire having a longer tip, which is flush with or projects less than for instance 0.5, 1 or 2 cm from the deformable member 63 if the deformable member is in uncompressed condition may be selected if the lesion is in a position where the blood vessel is relatively robust and/or has little curvature. Also the stiffness of the tip portion of the guidewire can be selected in accordance with cautiousness requirements at the location of the lesion.

Figure 7:
FIG. 7 is a side view in cross-section of a guidewire support system as shown in FIGS. 4-6 in a catheter sheath.

In FIG. 7, the support catheter 5 shown in FIGS. 4-6 is shown in a position inside a support and exchange tube 14. This support and exchange tube 14 can be slided over the support catheter 5 for providing further improved support and to further enhance centering of the guidewire end 9, 59 relative to the blood vessel 1. Furthermore, if the support and exchange tube 14 has been advanced until its distal end has reached the distal end 9, 59 of the guidewire 3, 53 or the distal end of the support catheter 5, the guidewire 3, 53 or, respectively, the support catheter 5 can be removed while maintaining a guide for guiding another implement to the position of the lesion 2. This is particularly advantageous if it is desired to exchange a guidewire 59 as shown in FIGS. 4-6 and/or the support catheter 5.

Figure 8:
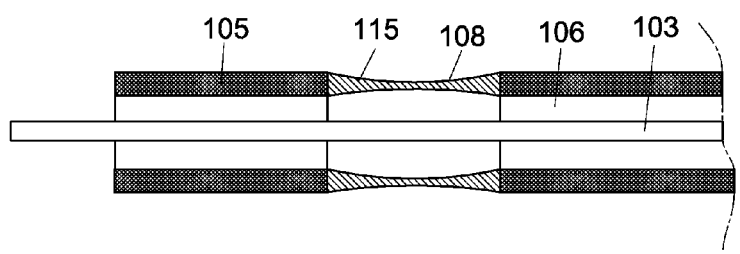
FIG. 8 is a side view in cross-section of a proximal end portion of a third example of a guidewire system according to the invention in a first operating condition.
Figure 9:
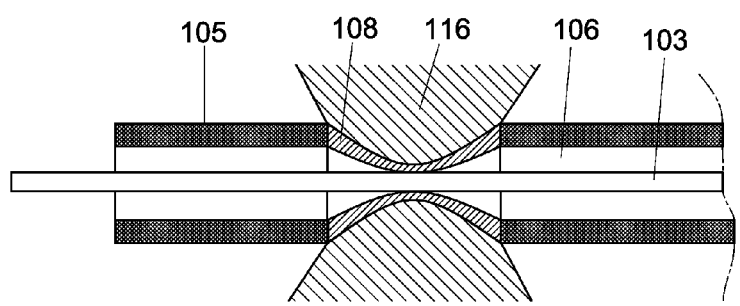
FIG. 9 is a side view in cross-section of the portion of the guidewire system shown in FIG. 8 in a second operating condition.

In FIGS. 8 and 9 a proximal end portion of yet another example of a guidewire system according to the invention is shown. According to this example, the guidewire support system has a guidewire engagement structure in the form of a displaceable support catheter wall portion 108. The support catheter wall portion 108 can be brought in clamping engagement with the guidewire, by clamping a torque steering device 116 (partially shown) or other clamp to the support catheter 105. The guidewire 103 may be a suitably dimensioned conventional guidewire 103 and the torque steering device 116 is to be a suitably dimensioned to clampingly engage the support catheter 105. By pressing the displaceable catheter wall portion 108 against the guidewire 103, the guidewire 103 can be held positioned in a fixed position in longitudinal direction relative to the support catheter 105. This allows to advance the support catheter 105 and the guidewire 103 simultaneously in a simple manner. By releasing the pressure of the displaceable catheter wall portion 108 against the guidewire 103, the guidewire 103 is released and can easily be advanced or retracted relative to the support catheter 105.

The displaceable support catheter wall portion 108 includes a flexible catheter wall portion 108 for transferring an externally applied clamping force at least partially (part of the pressure is used for the elastic deformation of the flexible catheter wall portion 108) to the guidewire 103 in the lumen 106. The pressing force is exerted by the torque steering device 116 clamping the guidewire 103 and the support catheter 105 against each other. Depending on the clamping forces exertable by the steering device, the catheter wall 105 may be flexible enough, so a special wall section more flexible than other wall sections, where the steering device is to be mounted can be dispensed with, provided the catheter wall is elastically deformable to a sufficient extent to substantially spring back to its original shape when the steering device releases the catheter.

Figure 10:
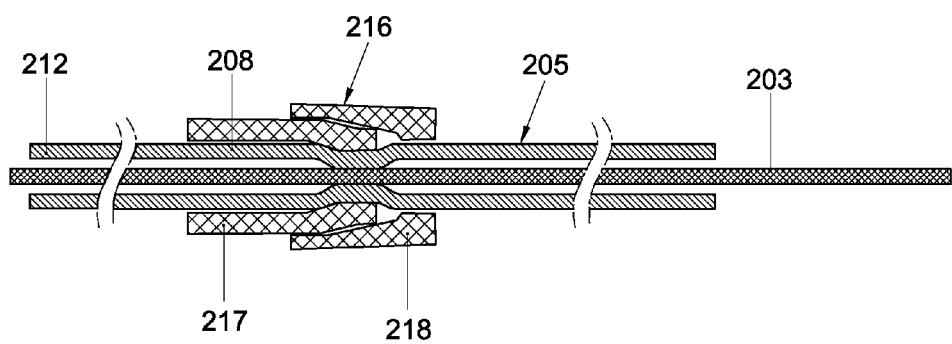
FIG. 10 is a side view in cross-section of a proximal end portion of a fourth example of a guidewire system according to the invention.

In FIG. 10, yet another example of a guidewire system according to the invention is shown. According to this example, the guidewire engagement structure for allowing and causing the support catheter to engage the guidewire is constituted by a torque steering device 216 and the wall 208 of the catheter, which is sufficiently elastically deformable to be pressed against the guidewire 203 for fixing the guidewire 203 relative to the support catheter 205 by the torque steering device 216 and to spring back so that the guidewire 203 is released when the clamping pressure is removed. The required flexibility of the catheter wall that allows the catheter wall to be pressed against the guidewire for fixing the guidewire and to fully release the guidewire when the clamping force is released is mainly achieved by selection of a suitable wall material as regards its specific material stiffness and deformability and a suitable wall thickness.

The elastically deformable wall material in the section of the support catheter to which the torque steering device may be clamped is preferably relatively soft polymeric and/or elastomeric material having hardness of less than 55 Shore D and preferably lees than 50 shore D. The polymeric and/or elastomeric material may for instance be or include polyamide, polyurethane or polyether block amide.

For combining easy radial compressibility of the support catheter to clampingly fix the guidewire with a high bending stiffness of a proximal portion of the support catheter that is to be held by the interventionist (for instance the most proximal 15-50 cm of the catheter), to allow accurate control over axial movements of the support catheter, axial reinforcements such as axially oriented fibers may be embedded in the wall of proximal portion of the support catheter that is to be held by the interventionist.

The torque steering device 216 is composed of a wedge member 217 that can be urged axially into a ring member 218 so that a resultant radial inward clamping force is exerted onto the catheter 205. To limit the extent to which the catheter wall material is deformed during clamping at a given inward radial displacement, it is preferred that the catheter wall is pressed towards and against the guidewire in not more than three and preferably not more than two locations circumferentially distributed and spaced about the catheter. Also in this embodiment, the guidewire 203 may be a conventional guidewire.

The catheter 205 has a proximal end portion 212 of preferably at least 5 cm length and more preferably at least 10 or 20 cm length, of which the diameter does not increase towards the proximal end. Thus a torque steering device such as the device 216 can easily be passed onto the catheter 205 from its proximal end, i.e. a proximal end portion of the support catheter can be threaded through the torque steering device until the torque steering device has reached a position spaced from the proximal end of the support catheter. This in turn allows the torque steering device 216 to be fixed in a more distal position than when a conventional catheter would de used, which is equipped with a hub so that the torque steering device would have to be fixed to the guidewire in a position proximal of the catheter. The more distal position of the torque steering device is advantageous for a more direct control over the orientation of the distal tip of the guidewire.

Placement of the torque steering device in a position distally spaced from the proximal end of the support catheter can also be facilitated by providing that the support catheter is packaged with the torque steering device pre-mounted to a proximal end portion of the support catheter. The presence of a hub at the proximal end of the support catheter does then not interfere with positioning the torque steering device in a position spaced from the proximal end of the support catheter and the hub. Furthermore, the need of manipulating the support catheter for mounting the torque steering device thereto outside the sterile environment in which it has been packaged is avoided.

Since the torque steering device can be clamped to the support catheter in several positions at different distances spaced from the proximal end of the support catheter (and/or of a hub at the proximal end, if any), it is possible to axially hold the guidewire relative to the support catheter in a position close to an opening in the skin of the patient where the guidewire and the support catheter enter the patient, so that a particularly direct control over the guidewire, both in longitudinal direction and in rotational sense about its longitudinal axis is achieved. Furthermore, in released condition, the torque steering device can be repositioned as the guidewire and the support catheter are inserted further into the patient. To maintain control over the position of the guidewire relative to the support catheter as the torque steering device is released and displaced to another clamping position, a second torque steering device may be clamped to the support catheter prior to releasing the first torques steering device to maintain the guidewire fixed relative to the support catheter as the first torque steering device is released and displaced. After the first torque steering device has been clamped to the support catheter causing the guidewire to be fixed relative to the support catheter in the new position, the second torque steering device can be released again.

If a section of the support catheter wall portion is provided that is more flexible than longitudinally adjacent sections of the support catheter wall, to facilitate clamping the guidewire by pressing the support catheter wall against the guidewire extending through the support catheter, the length of the relatively flexible support catheter wall section wall is preferably such that the torque steering device can be clamped thereto in several positions at different distances from the proximal end. Alternatively, or in addition, a plurality of relatively flexible catheter wall sections spaced apart in longitudinal direction, with less flexible catheter wall section located in-between, can be provided.

Within the framework of the invention as set forth in the claims, many other variations and applications than those described as examples are conceivable. For instance, the guidewire can be introduced in preparation of delivery of other items than stents, such as heart valves. Furthermore, the support catheter may also constitute a delivery catheter, so that the interventional device, such as a dilatation balloon and a stent, are delivered directly to the location of the stenosis as the guidewire and the support catheter are advanced to that position.

For torsional stiffness and easy rotation about its longitudinal axis, the support catheter is preferably circumferentially closed over at least a portion, preferably most) of its length, i.e. preferably not of the type having a longitudinal cut from its proximal end to its distal end for "short wire capability".

Suitably dimensioned embodiments of a guidewire system according to the invention may also be used for other endovascular applications and neurovascular applications.

The invention may also be embodied in a method for bringing a guidewire in a predetermined position crossing a stenosis in a vessel of a patient, the method comprising bringing a guidewire and a support catheter to a position near the stenosis, the support catheter bounding a lumen through which the guidewire extends for receiving at least a portion of the guidewire, wherein at least the guidewire comprises a support catheter engagement structure for engaging the support catheter inside the lumen or the support catheter comprises a guidewire engagement structure for engaging the guidewire inside the lumen, the engagement structure in engaged condition causing the guidewire and the support catheter to be held mutually positioned in longitudinal direction thereof.

The invention claimed is:

1. A guidewire support system comprising a support catheter for insertion into a vascular system of a human or an animal, the support catheter bounding a lumen for receiving at least a portion of a guidewire, and comprising a guidewire engagement structure for allowing the support catheter to engage the guidewire inside the lumen, the engagement structure in engaged condition causing the guidewire and the support catheter to be held mutually positioned at least in longitudinal direction thereof, wherein the guidewire engagement structure includes: a support catheter wall portion sufficiently elastically deformable for transferring an externally applied clamping force at least partially to fix the guidewire in the lumen and to release the guidewire in response to releasing of the clamping force; and a torque steering device arranged to be clamped to an outside surface portion of the support catheter and for exerting a clamping force to the support catheter causing said wall portions of the support catheter to be clamped against the guidewire in the lumen, wherein the support catheter extends through the torque steering device, the torque steering device is displaceable in the longitudinal direction along a section of the support catheter, between different positions at different distances in the longitudinal direction from the proximal end of the support catheter where a wall portion of the support catheter is clampable against the guidewire by the torque steering device for effecting the fixation of the guidewire in the lumen.

2. A guidewire support system according to claim 1, wherein the torque steering device and the support catheter are arranged such that the torque steering device can be passed onto the support catheter from the proximal end of the support catheter.

3. A guidewire support system according to claim 1, wherein the guidewire engagement structure includes at least one displaceable support catheter wall portion that is more flexible than longitudinally adjacent wall portions of the support catheter.

4. A guidewire support system according to claim 1, wherein the guidewire engagement structure is constituted by a restriction of the lumen of the support catheter for engaging an abutment projecting transversely from the guidewire.

5. A guidewire support system according to claim 4, wherein the support catheter has a proximal end and a distal end, the abutment and the restriction being located closely adjacent to the distal end of the support catheter.

6. A guidewire support system according to claim 1, wherein the support catheter has a proximal end and a distal end, a distal end portion of the support catheter being constituted by a deformable member of a material softer than adjacent more proximal portions of the support catheter.

7. A guidewire support system according to claim 6, wherein the deformable member in non-deformed condition has an outer cross-sectional contour larger than the cross-sectional contour of a proximally adjacent portion of the support catheter.

8. A guidewire support system according to claim 6, wherein the deformable member is of natural and/or synthetic elastomeric material having a hardness of less than 60 Shore A.

9. A guidewire support system according to claim 1, wherein at least a portion of the support catheter closely adjacent to a distal tip is at least partially radiopaque.

10. A guidewire system including a guidewire support system according to claim 1 and a guidewire.

11. A guidewire system according to claim 10, wherein the guidewire engagement structure is constituted by a restriction of the lumen of the support catheter for engaging an abutment projecting transversely from the guidewire and wherein at least the guidewire comprises an abutment for engaging the restriction, the abutment being located on a distal side of the restriction.

12. A guidewire system according to claim 10, wherein the guidewire engagement structure is constituted by a restriction of the lumen of the support catheter for engaging an abutment projecting transversely from the guidewire and wherein at least the guidewire comprises an abutment for engaging the restriction, the abutment being located on a proximal side of the restriction.

13. A guidewire system according to claim 11, wherein the support catheter has a proximal end and a distal end, a distal end portion of the support catheter being constituted by a deformable member of a material softer than adjacent more proximal portions of the support catheter and wherein the distal end of the guidewire is inside the deformable member if the abutment contacts the restriction, and the deformable member is in undeformed condition.

14. A guidewire system according to claim 13, wherein the deformable member is elastically compressible in longitudinal direction to such an extent that, while the abutment contacts the restriction, the distal end of the guidewire projects from the deformable member.

15. A guidewire system according to claim 12, wherein the support catheter has a proximal end and a distal end, a distal end portion of the support catheter being constituted by a deformable member of a material softer than adjacent more proximal portions of the support catheter and wherein the distal end of the guidewire is inside the deformable member if the abutment contacts the restriction, and the deformable member is in undeformed condition.

16. A guidewire system according to claim 1, wherein the support catheter wall portion sufficiently elastically deformable for transferring an externally applied clamping force at least partially to fix the guidewire in the lumen and to release the guidewire in response to releasing of the clamping force has a hardness of less than 55 Shore D.

17. A guidewire system according to claim 1, wherein the support catheter wall portion sufficiently elastically deformable for transferring an externally applied clamping force at least partially to fix the guidewire in the lumen and to release the guidewire in response to releasing of the clamping force, includes a plurality of embedded axially oriented fibers.

18. A guidewire system according to claim 1, wherein the torque steering device comprises:
a ring member; and
a wedge member adapted and configured for axial advancement into the ring member, resulting in compression of the wedge member and a portion of the support catheter wall.

19. A guidewire system according to claim 1, wherein the wedge member is adapted and configured to press against the support catheter wall in no more than three points.

* * * * *